(12) United States Patent
Burbar et al.

(10) Patent No.: US 7,772,559 B2
(45) Date of Patent: Aug. 10, 2010

(54) METHOD FOR STABILIZING THE GAIN OF A PET DETECTION SYSTEM

(75) Inventors: Ziad Burbar, Knoxville, TN (US); James Corbeil, Knoxville, TN (US); Gregory Hayzen, Knoxville, TN (US); Sridhar Kuppuswamy, Knoxville, TN (US); Ralf Ladebeck, Erlangen (DE); Matthew Martin, Powell, TN (US); Matthias Schmand, Lenoir City, TN (US)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 12/232,451

(22) Filed: Sep. 17, 2008

(65) Prior Publication Data

US 2009/0114827 A1 May 7, 2009

(30) Foreign Application Priority Data

Sep. 20, 2007 (DE) .................... 10 2007 044 873

(51) Int. Cl.
*G01T 1/164* (2006.01)
(52) U.S. Cl. ............................................. 250/363.03
(58) Field of Classification Search ............. 250/363.03
See application file for complete search history.

(56) References Cited

U.S. PATENT DOCUMENTS 6,313,459 B1 * 11/2001 Hoffe et al. ............. 250/214 R
7,218,112 B2   5/2007 Ladebeck
7,488,943 B2 * 2/2009 Rose et al. ............. 250/363.04
2004/0071259 A1  4/2004 Lacey
2005/0138934 A1 * 6/2005 Weigert et al. ................. 62/3.2

OTHER PUBLICATIONS

P. Crespo, M. Kapusta, J. Pawelke, M. Moszyński, and W. Enghardt, "First In-Beam PET Imaging With LSO/APD Array Detectors," IEEE Transactions on Nuclear Science (Oct. 2004) vol. 51, No. 5, pp. 2654-2661, DOI: 10.1109/TNS.2004.835780.*
Spanoudaki, V. u.a., "Effect of Temperature on the Stability and Performance of an LSO-APD PET Scanner", IEEE Nuclear Science Symposium Conference Record. 2005, vol. 5, S.3014-3017; Others.

* cited by examiner

*Primary Examiner*—Constantine Hannaher
(74) *Attorney, Agent, or Firm*—Harness, Dickey & Pierce, P.L.C.

(57) ABSTRACT

A method for stabilizing the gain of a PET detection system with a cooling unit includes: determining the temperature of at least one component of the PET detection system, comparing the actual gain with a reference value, and actuating the cooling unit to influence the temperature such that the gain tends to the reference value. In at least one embodiment, the reference value is determined by determining the temperature of the at least one component during a test measurement, determining the gain during the test measurement, determining a functional dependence of the gain on the temperature, and selecting the reference value based on the gain to be stabilized. Advantageously, in at least one embodiment the gain can be kept constant using the described method in a simple manner, with the influence of the temperature of the components being taken into account.

20 Claims, 2 Drawing Sheets

METHOD FOR STABILIZING THE GAIN OF A PET DETECTION SYSTEM

PRIORITY STATEMENT

The present application hereby claims priority under 35 U.S.C. §119 on German patent application number DE 10 2007 044 873.4 filed Sep. 20, 2007, the entire contents of which is hereby incorporated herein by reference.

FIELD

Embodiments of the present invention generally relate to a method for stabilizing the gain of a PET detection system and a detection system for positron emission tomography.

BACKGROUND

In recent years, the use of both positron emission tomography (PET) and magnetic resonance imaging (MRI) for medical diagnosis has become more widespread. While MRI is an imaging method for displaying structures and slice images in the interior of the body, PET allows visualizing and quantifying of metabolic activities in vivo.

PET uses the particular properties of positron emitters and positron annihilation to quantitatively determine the function of organs or regions of cells. Appropriate radiopharmaceuticals marked with radionuclides are administered to the patient before the examination. When the radionuclides decay, they emit positrons which within a short distance interact with an electron and this results in a so-called annihilation. This creates two gamma quanta which fly apart in opposite directions (offset by 180°). The gamma quanta are detected by two PET detector modules lying opposite one another within a particular time frame (coincidence measurement), as a result of which the location of the annihilation is determined to be at a position along the connecting line between these two detector modules.

For the purpose of detection, the detector module in PET must in general cover a large portion of the gantry arc length. It is subdivided into detector elements with a side length of a few millimeters. Each detector element generates an event record specifying the time and detection location, that is to say the corresponding detector element, if it detects a gamma quantum. This information is transmitted to a fast logic and compared. If two events coincide within a maximum period of time, a gamma decay process is assumed to have occurred on the connecting line between the two corresponding detector elements. A tomography algorithm, that is to say the so-called back projection, is used to reconstruct the PET image.

U.S. Pat. No. 7,218,112 B2 discloses a combined PET/MRI system which uses lutetium oxyorthosilicate (LSO) as a scintillation crystal for converting the gamma quanta into light and uses avalanche photodiodes (APD) for detecting the light. The photodiodes are connected to preamplifiers.

The gain of commonly used semiconductor amplifiers and semiconductor detectors (avalanche photodiodes, APD) in particular depends on the temperature. Since the components are subjected to temperature variation, in particular heating, during operation, cooling is necessary. The temperature of the amplifiers and photodiodes can be controlled globally by supplying cooled air. When using air with a constant temperature, the temperature of the amplifiers results from the balance of the generated heat and the heat emitted through the air via the surfaces of the amplifiers. The cooling can be used in the same fashion for other parts of the detection system.

Spanoudaki et al., "Effect of Temperature on the Stability and Performance of an LSO-APD PET Scanner", IEEE Nuclear Science Symposium Conference Record 2005, 3014-3017 investigated the temperature stability of the LSO APDs of a PET system. The influence of different temperature sources on different components of the PET system is analyzed therein. By way of example, the gain of the APD depends on the temperature, as does the position of the respective photopeak. By way of example, the temperature and the position of the photopeak over time are illustrated in a number of graphical illustrations. The change of the energy resolution with temperature is analyzed and statistics for the 256 examined detection modules are generated. In this case, the causes of the temperature increase are investigated and a prediction for the shift of the photopeak and energy resolution with increasing temperature is made.

US 20040071259 A1 discloses an x-ray detector with a thermoelectric cooling unit. Both active and passive cooling units are used in this case. A reference temperature is stabilized by controlling the power of the thermoelectric cooling unit by determining the temperature of the x-ray detector by way of temperature sensors.

It is disadvantageous in the case of the known solutions that the ability to control the temperature is insufficient if there are changes in the heat generation during operation. By way of example, if there is an increase in the generated heat or in the heat introduced from the outside (for example by turbulence in the RF screen induced by gradients), then the gain will change despite the cooling because the above-mentioned balance has shifted. Furthermore, there are typically different sources which input heat. This input of heat results in a spatial and temporal temperature distribution. This can result in the temperature-dependent components such as APDs and preamplifiers having a different temperature. Due to the fact that it is typically not possible to directly measure the temperature of the critical components, and that a plurality of components influence the gain of the overall chain via their temperature dependence, the individual temperature profile must be inferred from spatially distributed temperature measurement points. As an alternative, it is possible to omit this intermediate step and directly determine the relationship with the gain.

SUMMARY

In at least one embodiment of the present invention, a method and a detection system are specified which have sufficient stability with regard to the gain.

According to one embodiment of the invention, a method for stabilizing the gain of an amplifier of a PET detection system with a cooling unit comprises:
  determining the temperature of at least one component of the PET detection system,
  calculating the actual gain from the determined temperature,
  comparing the actual gain with a reference value, and
  actuating the cooling unit to influence the temperature such that the actual gain tends to the reference value,
  wherein the reference value is determined by a method comprising the following method steps:
  determining the temperature of the at least one component during a test measurement,
  determining the gain during the test measurement,
  determining a functional dependence of the gain on the temperature, and
  selecting the reference value based on the gain to be stabilized.

This embodiment of the method is particularly advantageous in that it automatically reacts to changes in the temperature, and in that the actual temperature is determined by components of the detection system. As a result of this, temperature-dependent influences of different components on the gain of the detection system can be taken into account in the control. A measurement of the gain and its change with temperature is not required during operation, since this relationship was already determined in the previous test measurement. It is then possible always to infer the actual gain from the determined temperature, and to control the cooling unit in the case of deviation from the reference value.

Alternatively it is possible to use the gain as the variable to be controlled and fix an appropriate reference value. However, this has the disadvantage that the gain has to be determined a number of times during an examination, and the PET system is then not available. The dead time created in this way reduces the through-put of examinations.

In an advantageous refinement of the method, the temperature of a plurality of components of the PET detection system is determined, and an overall value is determined from the temperatures. The overall value is compared to the reference value. The temperatures of the plurality of components in the test measurement and a functional dependence of the gain on the temperatures are determined to establish the reference value. The gain can be determined from the measured temperatures with high precision because a multiplicity of influences can be taken into account.

A method is advantageous if, in order to determine the reference value, the temperatures are combined in a matrix and weighting factors which describe the dependence of the gain on the temperatures are determined by principal component analysis and linear regression. The influence of the temperature of the components on the gain can be easily taken into account in this way.

In an advantageous refinement of an embodiment of the invention, the temperatures of a plurality of components are determined over time in order to determine the reference value, the gain is determined over time, and determining the functional dependence of the gain on the temperature comprises:

combining in a matrix T the temperatures over time of the components, performing principal component analysis on the matrix T, and determining coefficients k which satisfy the equation $V_t = k \times O$, where $V_t$ is the gain over time.

This affords an efficient possibility for taking into account the temperatures of a plurality of components. In this embodiment, the matrix represents the overall value.

BRIEF DESCRIPTION OF THE DRAWINGS

Further advantages and refinements of the invention emerge from the example embodiments described below in combination with the figures, in which.

DETAILED DESCRIPTION OF THE EXAMPLE EMBODIMENTS

Figure 1:
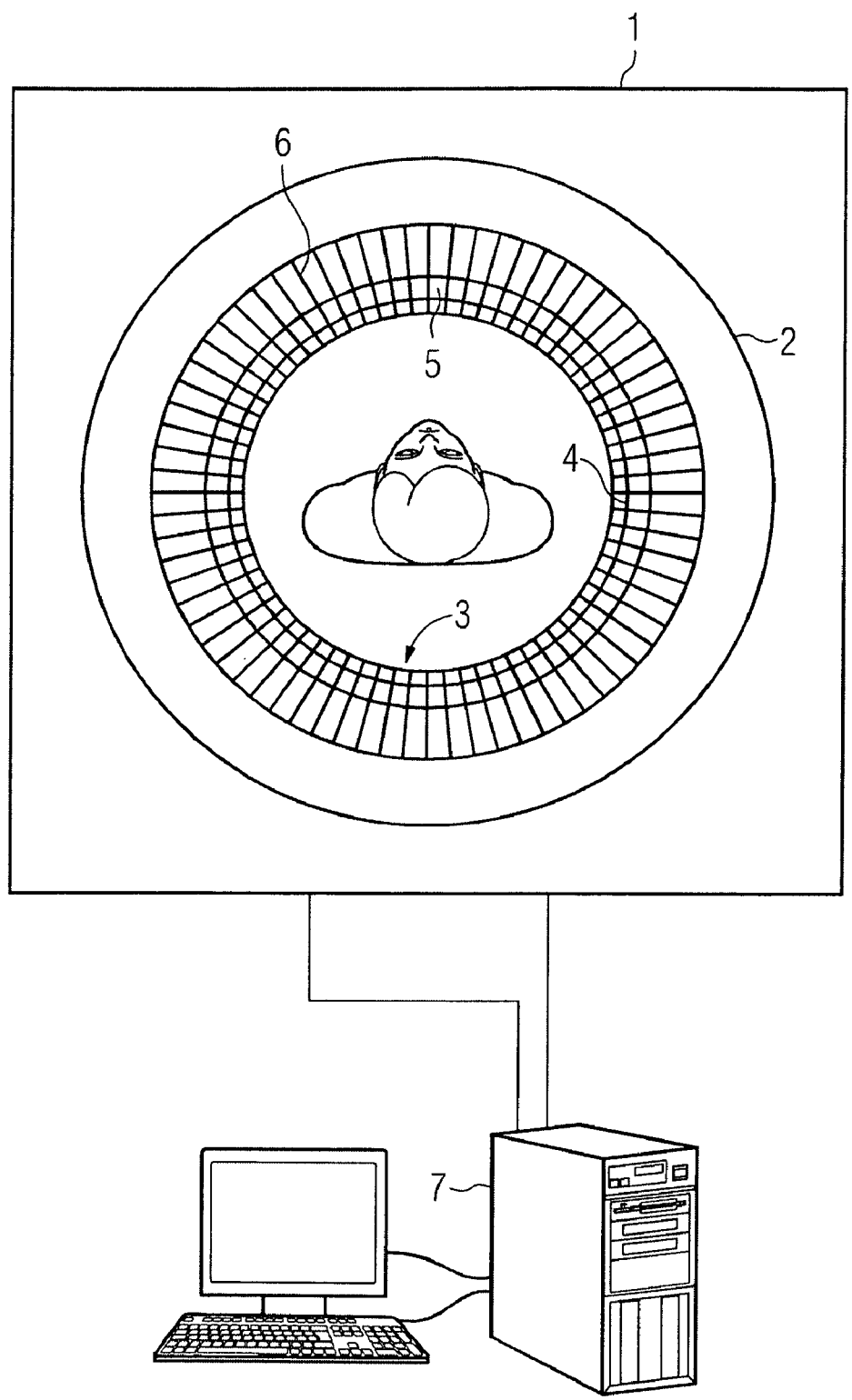
FIG. 1 shows a schematic illustration of a combined MRI/PET scanner.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The example embodiments of the invention can preferably be applied to a combined MRI/PET scanner. A combined scanner can advantageously acquire both MRI and PET data isocentrically. This makes it possible to precisely define the examination volume within the region of interest using the data of the first modality (PET), and use this information in the further modality (e.g. magnetic resonance imaging). Transferring the volume information of the region of interest from an external PET scanner to an MRI scanner is possible, but there is increased complexity involved in registering the data.

In general, all data which can be determined by magnetic resonance imaging or another imaging method can be detected in the selected region of interest in the PET data record. By way of example, rather than acquiring spectroscopy data, it is also possible to acquire fMRI data, diffusion maps, T1 or T2 weighted images, or quantitative parameter maps by way of magnetic resonance imaging examinations of the region of interest. It is also possible to use computed tomography methods (for example, perfusion measurements, multi-energy imaging) or x-rays. The advantage of the described method is that in each case the region of interest can be narrowed down very effectively to a specifically occurring pathology of the patient by way of the PET data record.

Additionally, however, it is also possible to display various biological characteristics in the PET data record by using a plurality of so-called tracers, and thus to further optimize the region of interest and the volume thereby determined, or to select a number of different examination volumes at once which are then analyzed in subsequent examinations.

FIG. 1 shows a known apparatus 1 for superposed MRI and PET imaging. The apparatus 1 comprises a known MRI tube 2. The MRI tube 2 defines a longitudinal direction z, which extends orthogonally to the plane of the drawing of FIG. 1.

As can be seen in FIG. 1, a plurality of PET detection units 3 arranged opposite to one another in pairs about the longitudinal direction z are arranged coaxially within the MRI tube 2. The PET detection units 3 preferably include an APD photodiode array 5 with an upstream array of LSO crystals 4 and an electrical amplifier circuit (AMP) 6. However, embodiments of the invention are not limited to the PET detection units 3 with the APD photodiode array 5 and the upstream array of LSO crystals 4, but rather differently designed photodiodes, crystals and apparatuses can equally be used for detection.

The image processing for superposed MRI and PET imaging is carried out by a computer 7.

The MRI tube 2 defines a cylindrical first field of view along its longitudinal direction z. The multiplicity of PET detection units 3 define a cylindrical second field of view along the longitudinal direction z. According to an embodiment of the invention, the second field of view of the PET detection units 3 substantially corresponds to the first field of view of the MRI tube 2. This is implemented by correspondingly matching the arrangement density of the PET, detection units 3 along the longitudinal direction z.

Figure 2:
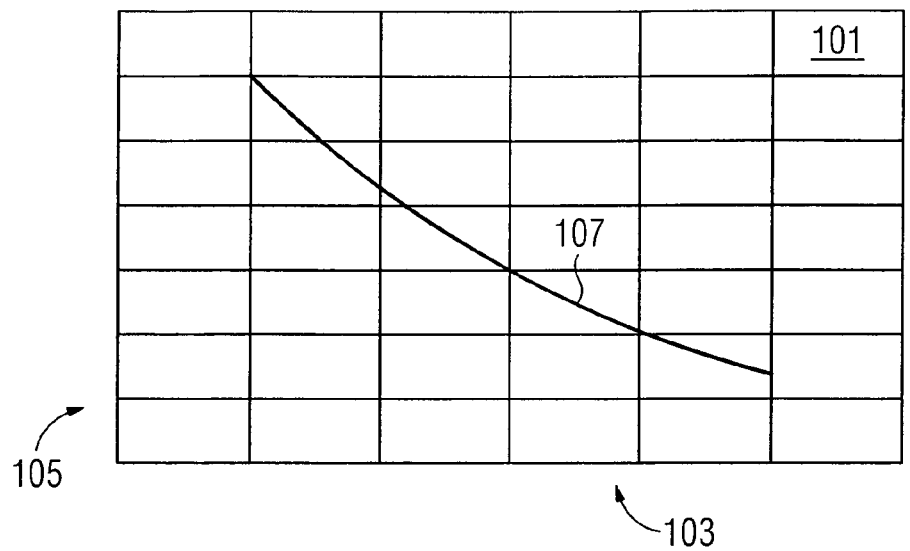
FIG. 2 shows an example relationship between gain and temperature.

FIG. 2 shows in an example manner the change of the gain with temperature in a diagram 101. Temperature is plotted along the horizontal axis 103 of the diagram 101. The vertical axis 105 represents the gain. A typical curve 107 schematically illustrates the temperature dependence of the gain. The gain decreases as the temperature increases. The gain is intended to be kept as constant as possible in order to obtain reproducible measurement values, which can be achieved by stabilizing the temperature. However, for this it is necessary to know the influence of individual components of the detection system on the gain.

Figure 3:
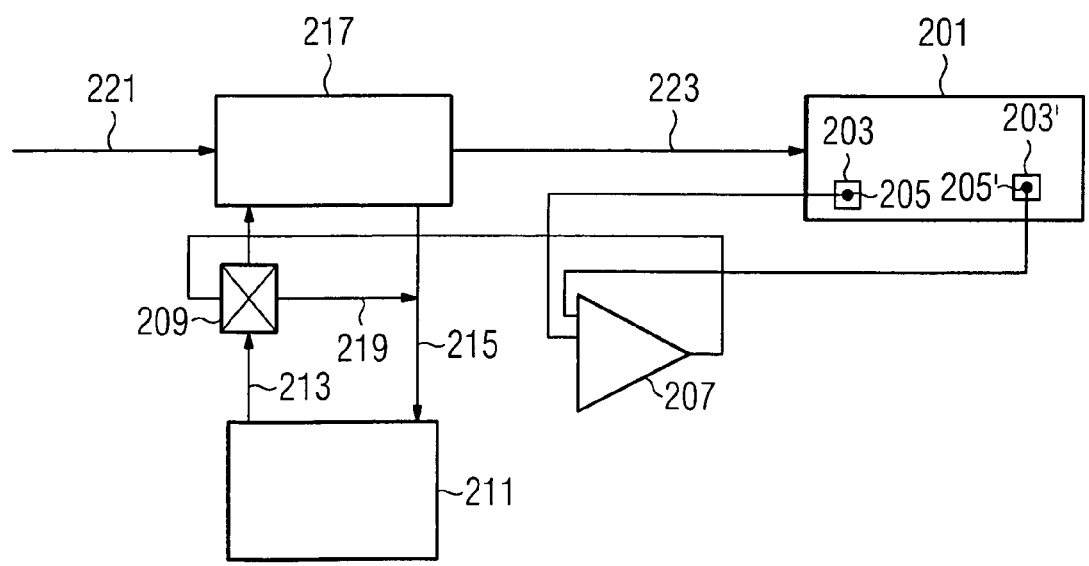
FIG. 3 shows a schematic illustration of an example embodiment of a detection system.

FIG. 3 schematically illustrates a detection system of an example embodiment of the invention. It includes a PET detector 201, which in turn comprises a plurality of components 203 and 203'. By way of example, these can be a scintillation crystal, a photodiode and a preamplifier with a temperature-dependent gain. The components 203 and 203' are provided with temperature sensors 205 and 205', by which the temperature of the components 203 and 203' can be measured.

In general, the PET detector 201 includes further components which are not illustrated here. It is not necessary for all components to be provided with temperature sensors. The temperature sensors 205 and 205' are connected to a control unit 207 which is provided to actuate a three-way valve 209. A cooling assembly 211 is fluid-connected to a heat exchanger 217 via two lines 213 and 215. Cooled water can flow through line 213 from the cooling assembly 211 to the heat exchanger 217. Water heated in the heat exchanger 217 flows back into the cooling assembly 211 via line 215 for renewed cooling. The three-way valve 209 is arranged in the line 213 and can regulate the inflow of cooled water into the heat exchanger 217 from the cooling assembly 211. A line 219 which leads to the line 215 from the three-way valve 209 is provided for this purpose. Hence a diversion of cooled water via the three-way valve 209 is possible, as a result of which the cooling power of the heat exchanger is decreased. The water flow can also be completely diverted from the heat exchanger.

The heat exchanger 217 is designed such that surrounding air can be cooled by heat exchange using the cooled water. For this purpose, the surrounding air is guided into the heat exchanger 217 using a fan (not illustrated). This is illustrated schematically by the arrow 221. By way of a fan (likewise not illustrated), the cooled air can be supplied to the PET detector 201, as a result of which the latter can be cooled. This is illustrated schematically by the arrow 223.

Cooling is performed by the control unit 207 and by actuating the three-way valve 209, and the regulation of the cooling power in the heat exchanger 217 accompanying this. The control signal is calculated by the control unit 207 by way of the read-out temperatures of the temperature sensors 205 and 205' of the components 203 and 203', and the three-way valve 209 is actuated accordingly.

There are a number of alternatives for determining a control signal for the three-way valve 209. First of all, it is possible to control the measured temperature directly. Consequently, more cooling water will be fed to the heat exchanger 217 from the cooling assembly 211 if the temperature has risen, so that colder air is available for cooling the PET detector 201.

However, since the temperature of the PET detector 201, or its components 203 and 203', is only important due to its influence on the gain, the gain is calculated from the measured temperatures of the components 203 and 203' in an alternative embodiment. For this purpose it is advantageous to carry out calibration measurements in order to precisely determine the relationship between the temperatures and the gain. Then the actual gain can always be determined and compared to a reference value, which results in an error signal. In the case of a non-zero error signal, the three-way valve 209 is correspondingly actuated to increase or decrease the temperature of the air. In this context it is particularly advantageous that it is possible to react to gain variations in the fastest possible way during the use of the PET/MRI scanner.

It is also possible that the temperature of one component 203 or 203' is sufficient for control. This depends in particular on the construction of the PET detector 201 and the influence of the temperature of the component 203 or 203 on the gain resulting therefrom. Likewise, it may be necessary to take into account the temperatures of a number of components.

In particular in the latter case it is advantageous if the temperature sensors 205 and 205' are positioned at locations in the PET detector 201 where there is a large energy conversion. By way of example, these can be the inlet and outlet opening of the cooled air or the surface of the PET detector 201.

Weighting factors for the respective temperature sensor 205 and 205' can be determined by principal component analysis and linear regression, which are correspondingly included in the control signal. For this purpose, the temperatures over time of the components to be taken into account are acquired during simulated use of the MRI/PET scanner in calibration measurements. The variation of gain over time is also determined. The temporal profiles $T_1$ to $T_n$ of the n components are combined in a matrix T and the temporal profile of the gain is illustrated as a vector $V_t$. The matrix T is subjected to principal component analysis. Consequently, the vectors describing the variance are available as new basis vectors of an orthogonal matrix O. A linear regression is now used to determine coefficients k, which satisfy the following equation:

$$V_t = k \times O.$$

As a result, the relationship between the present gain and the prevailing temperature of the components is established and it has been made possible to stabilize the gain by controlling the temperature.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for stabilizing the gain of a PET detection system with a cooling unit, comprising:
   determining a temperature of at least one component of the PET detection system;
   calculating an actual gain from the determined temperature;
   comparing the actual gain with a reference value; and
   actuating the cooling unit to influence the temperature based on the comparison between the actual gain and the reference value such that the actual gain tends to the reference value, the cooling unit having variable cooling power; wherein the reference value is determined by:
      determining the temperature of the at least one component during a test measurement,
      determining the gain during the test measurement,
      determining a functional dependence of the gain on the temperature, and
      selecting the reference value based on the gain to be stabilized.

2. The method as claimed in claim 1, wherein the temperatures of a plurality of components are determined over time in order to determine the reference value, the gain is determined over time, and the determining of the functional dependence of the gain on the temperature by:
   combining in a matrix T the temperatures over time of the plurality of components,
   performing principal component analysis on the matrix T, and
   determining coefficients k which satisfy the equation $V_t = k \times O$, where $V_t$ is the gain over time.

3. The method as claimed in claim 2, wherein the PET detection system has at least one temperature sensor for determining the temperature.

4. The method as claimed in claim 2, wherein the temperature is measured at a surface of the PET detection system.

5. The method as claimed in claim 2, wherein the temperature of a coolant of the cooling unit is determined before it enters the PET detection system.

6. The method as claimed in claim 5, wherein the temperature of the coolant is determined after leaving the PET detection system.

7. The method as claimed in claim 2, wherein the ambient temperature of the PET detection system is determined.

8. A tangible computer readable medium including program segments for, when executed on a computer device, causing the computer device to implement the method of claim 2.

9. The method as claimed in claim 1, wherein the PET detection system has at least one temperature sensor for determining the temperature.

10. The method as claimed in claim 1, wherein the temperature is measured at a surface of the PET detection system.

11. The method as claimed in claim 1, wherein the temperature of a coolant of the cooling unit is determined before it enters the PET detection system.

12. The method as claimed in claim 11, wherein the temperature of the coolant is determined after leaving the PET detection system.

13. The method as claimed in claim 1, wherein the ambient temperature of the PET detection system is determined.

14. A tangible computer readable medium including program segments for, when executed on a computer device, causing the computer device to implement the method of claim 8.

15. The method of claim 1, wherein the cooling unit includes a control unit configured to control the variable cooling power of the cooling unit.

16. The method of claim 1, wherein the functional dependence of the gain on the temperature is described by weighting factors associated with each of a plurality of temperature sensors for sensing a temperature of a component of the PET detector.

17. The method of claim 16, wherein the weighting factors are determined by principal component analysis and linear regression.

18. The method of claim 1, wherein a measurement of the gain and a change in the gain with temperature is not required during operation of the PET detector.

19. The method of claim 1, wherein the gain and a change in the gain with temperature is not measured during operation of the PET detector.

20. The method of claim 1, wherein temperatures of a plurality of components are determined over time in order to determine the reference value, the gain is determined over time, and the functional dependence of the gain is based on weighting factors associated with the plurality of components and variances of temporal profiles of the components.

* * * * *